US008343722B2

(12) United States Patent
Calistri et al.

(10) Patent No.: US 8,343,722 B2
(45) Date of Patent: Jan. 1, 2013

(54) METHOD FOR THE IDENTIFICATION OF COLORECTAL TUMORS (75) Inventors: Daniele Calistri, Forli (IT); Claudia Rengucci, Forli (IT)

(73) Assignee: Istituto Oncologico Romagnolo Cooperativa Sociale a.r.l., Forli (IT)

( * ) Notice: Subject to any disclaimer, the term of this patent is extended or adjusted under 35 U.S.C. 154(b) by 0 days.

(21) Appl. No.: 10/547,669

(22) PCT Filed: Feb. 27, 2004

(86) PCT No.: PCT/EP2004/001997
§ 371 (c)(1),
(2), (4) Date: Sep. 2, 2005

(87) PCT Pub. No.: WO2004/079004
PCT Pub. Date: Sep. 16, 2004

(65) Prior Publication Data
US 2006/0216713 A1 Sep. 28, 2006

(30) Foreign Application Priority Data

Mar. 7, 2003 (IT) .............................. MI2003A0434

(51) Int. Cl.
*C12Q 1/68* (2006.01)
*C12P 19/34* (2006.01)
*C07H 21/04* (2006.01)
(52) U.S. Cl. ................... 435/6.12; 435/91.2; 536/24.33
(58) Field of Classification Search ........................ None
See application file for complete search history.

(56) References Cited

U.S. PATENT DOCUMENTS

| 5,723,298 A | 3/1998 | Oommen et al. |
| 5,811,239 A | 9/1998 | Frayne |
| 6,114,124 A * | 9/2000 | Albertsen et al. ............... 435/7.1 |
| 6,482,803 B1 | 11/2002 | Roth et al. |

FOREIGN PATENT DOCUMENTS

| JP | 2001-128685 | 5/2001 |
| WO | WO 95/32731 | 12/1995 |
| WO | WO 99/06598 | 2/1999 |
| WO | WO 00/58514 | 10/2000 |
| WO | WO 01/18252 | 3/2001 |
| WO | WO 01/42502 | 6/2001 |
| WO | WO 01/42504 | 6/2001 |
| WO | WO 01/73002 | 10/2001 |
| WO | WO 02/092858 | 11/2002 |

OTHER PUBLICATIONS

Hayes et al., Identification of Sequence Motifs Responsible for the Adhesive Interaction between Exon v10-containing CD44 Isoforms, 2002, The Journal of Biological Chemistry vol. 277, No. 52, Issue of Dec. 27, pp. 50529-50534.*
Tian et al., Capillary and Microchip Electrophoresis for Rapid Detection of Known Mutations by Combining Allele-specific DNA Amplification with Heteroduplex Analysis, Clinical Chemistry 47:2, 173-185 (2001).*
Buck et al., Design Strategies and Performance of Custom DNA Sequencing Primers, BioTechniques 27:528-536 (Sep. 1999).*
Zhou et al., Counting alleles to predict recurrence of early-stage colorectal cancers, The Lancet • vol. 359 • Jan. 19, 2002 • www.thelancet.com.*
Calistri et al., "Detection of Colorectal Cancer by a Quantitative Fluorescence Determination of DNA Amplification in Stool", Neoplasia, vol. 6, No. 5, Oct. 2004, pp. 536-540.*
Zou et al., "A Sensitive Method to Quant!ify Human Long DNA in Stool: Relevance to Colorectal Cancer Screening", Cancer Epidemiol. Biomarkers, Prey. 2006; 15(6) , Jun. 2006.*
Ahlquist et al., "Colorectal Cancer Screening by Detection of Altered Human DNA in Stool: Feasibility of a Multitarget Assay Pane~", Abstract, Gastroenterology, vol. 119, Issue 5, p. 1219, Nov. 1, 2000, www..~astrojournal.org/article/PIISOO16508500895268/abs~rac t?bro~se volum.*
Srivastava et al. (Eds.) Molecular Pathology of Early Cancer, IOS Press, 1999, Chapter 2, p. 13.*
Wakamatsu et al., Frequent Expression of p53 Protein without Mutation in the a typical Epithelium of Human Bronchus, American Journal of Respiratory Cell and Molecular Biology vol. 21 1999, pp. 209-215.*
Kim et al. Higher indidence of p53 mutation . . . , European Journal of Obstetrics & Gynecology and Reproductive Biology 98 (2001) pp. 213-218.*
Tamura et al., Mutations of the APC Gene Occur during Early Stages of Gastric Adenoma Development, Cancer Res 1994;54:1149-1151. Published online Mar. 1, 1994.*
Wang et al., Prevalence of somatic alterations in the colorectal cancer cell genome, 3076-3080 _ PNAS _ Mar. 5, 2002 _ vol. 99 _ No. 5.*
GENBANK, Accession No. AC008575, Jul. 20, 2001, p. 1.*
Arakawa et al., Analysis of polymerase chain reaction products by highperformance liquid chromatography with fluorimetric detection and its application to DNA diagnosis, Journal of Chromatography B, 716 (1998) 119-128.*
Ahlquist D A et al: "Colorectal Cancer Screening by Detection of Altered Human DNA in Stool: Feasibility of a Multitarget Assay Panel" Gastroenterology, W.B. Saunders Company, Philadelphia, US, vol. 119, No. 5, Nov. 2000, pp. 1219-1227, XP001118414 ISSN: 0016-5085.
Rengucci C et al: "Multiple detection of genetic alterations in tumors and stool." Clinical Cancer Research: an Official Journal of the American Association for Cancer Research. Mar. 2001, vol. 7, No. 3, Mar. 2001, pp. 590-593, XP002286121 ISSN: 1078-0432.
Calistri, Daniele et al., "Detection of Colorectal Cancer by a Quantitative Fluorescence Determination of DNA Amplification in Stool", Neoplasia, 2004, pp. 536-540, vol. 6, No. 5.
Loktionov, Alexandre, Cell Exfoliation in the Human Colon: Myth, Reality and Implications for Colorectal Cancer Screening, Int J Cancer, 2007, pp. 2281-2289, vol. 120, Wiley-Liss, Inc.
Gerard, Christopher J. et al., "Improved Quantitation of Minimal Residual Disease in Multiple Myeloma Using Real-Time Polymerase Chain Reaction and Plasmid-DNA Complementarity Determining Region III Standards", Cancer Research, Sep. 1, 1998, pp. 3957-3964, vol. 58.
Schneeberger, Christian et al., "Quantitative Detection of Reverse Transcriptase-PCR Products by Means of a Novel and Sensitive DNA Stain", Genome Research, 1995, pp. 234-238, vol. 4, Cold Spring Harbor Laboratory Press.

* cited by examiner

*Primary Examiner* — Angela M Bertagna
(74) *Attorney, Agent, or Firm* — Young & Thompson (57) ABSTRACT

Disclosed is a method for the early diagnosis of colorectal carcinoma and determination of pre-cancerous lesions of the colon and rectum based on quantitation of DNA extracted from stool and amplified by PCR techniques.

3 Claims, 4 Drawing Sheets

Fig. 2c p53 curve

APC 1-2 curve

APC 3-4 curve

Fig. 3

METHOD FOR THE IDENTIFICATION OF COLORECTAL TUMORS

This invention relates in general to the diagnosis of tumours in human patients and animals. Specifically, it provides a method and kit for the early diagnosis of colorectal carcinoma and determination of pre-cancerous lesions of the colon and rectum. The method of the invention is based on quantitation of DNA extracted from stool and amplified with PCR techniques.

BACKGROUND OF THE INVENTION

In recent years, a great deal of information has been accumulated on the molecular alterations that take place during the development of tumors, such as gene mutations or genomic rearrangements, highlighting the possibility of detecting tumor alterations in biological fluids and consequently indicating the use of these markers as a valid non invasive diagnostic approach.

A tumor that has been widely investigated with this approach is colorectal cancer, which is one of the most common forms of cancer worldwide, with a clinical outcome varying considerably according to the type of lesion and stage of disease at diagnosis (1-3). An early diagnosis is fundamental to reduce morbidity and mortality as a high percentage of patients diagnosed in the early stages of disease are long-term survivors (4). Moreover, the possibility of detecting pre-malignant lesions makes this tumor an ideal target for screening programs. However, although several screening methods are available, a high percentage of individuals do not participate in colorectal cancer screening programs. There are many reasons for this low compliance, such as a lack of knowledge of the benefits of the available screening methods, especially colonoscopy, as well as the unpleasant and troublesome procedures (5).

Gene mutations in stool, especially K-ras (6-12) and to a lesser extent p53 (13), APC gene (14,15) and microsatellite instability (16), have been repeatedly investigated. Results have shown the presence of these molecular alterations in stool in only a fraction of patients, due to the relatively low frequency of single marker alterations in colorectal cancer. Multiple mutations have been analyzed in parallel on the same stool sample and this approach has led to improved test sensitivity, but is expensive, time-consuming and cannot easily be applied to screening programs (17-21).

The diagnostic potential of DNA amplification of exfoliated cells in stool has recently been considered. Preliminary evidence (19-21) has shown that the semi-quantitative evaluation of DNA amplification (L-DNA) of some DNA fragments longer than 200 bp detects more than 50% of colorectal cancers, with a very high specificity.

US application No. 20020004206 discloses a genetic assay for identifying a tumor disease from samples containing exfoliated epithelial cells. The patent application describes an assay comprising a step of PCR amplification of Kras, APC and p53 fragments, followed by semi-quantitative determination of the amplified DNA based on gel-staining.

DESCRIPTION OF THE INVENTION

The present invention is based on a novel, accurate and rapid approach to cancer detection, that allows a better discrimination between affected and non-affected individuals.

Specifically, object of the invention is a method for the quantitation of DNA from stool samples, useful for the early diagnosis of tumours and pre-cancerous lesions of the colon and rectum, which comprises the following steps:
1) DNA extraction from stool samples;
2) PCR amplification of at least three, preferably at least eight different DNA fragments with a length exceeding 100 base pairs, using deoxynucleotide triphosphates or primers labelled with detectable molecules;
3) quantitation of the amplified fragments (amplicons);
4) calculation of the total quantity of different amplicons;
5) comparison of the values obtained in (4) with a reference value.

The DNA extraction can be conducted by conventional techniques, using commercially available kits. The DNA fragments amplified in step (2) can span one or more non-overlapping genome regions, including genes and non-coding sequences, provided that the fragment length exceeds 100 by (base pairs), preferably between 100 and 1000 bp, and more preferably between 100 and 500 bp, The fragments can be amplified separately or simultaneously; in the latter case, the amplification products should be distinguished one another by means of appropriate labelling. For example, the primer oligonucleotides or deoxynucleotide tripliosphates used in the amplification reaction may carry detectable markers, such as fluorescent molecules (fluorochromes), preferably HEX™ (Applied Biosystems), 6-FAM™ (Applied Biosystems) and TAMRA™ (Applied Biosystems), or other molecules such as biotin, digoxigenin, fluorescein, rhodamine, Cy3, Cy5, 5-FAM NED™, VIC™ and PET™. The markers are chemically linked to one or more nucleotides within or at the ends of the primer sequences, preferably, on the first nucleotide residue, or to the deoxynucleotide triphosphates present in the PCR reaction mixture.

In a preferred embodiment, the following genome fragments are amplified: exons 5 to 8 of p53 (Gene Bank no. X54156, nt. 13042-13253, 13308-13489, 13986-14124, 14404-14603); genomic regions coding for aminoacids 862-954, 1035-1130, 1288-1402 and 1421-1515 of APC (exon 15-Gene Bank AF127506, M74088).

In a further preferred embodiment, the amplification products are quantified by automatic DNA sequencers/analysers, preferably using the 3100 Avant Genetic Analyzer® (Applied Biosystems). Other techniques suitable for fragment amplification according to the invention include immunoenzymatic techniques, real time PCR and chemiluminescence techniques.

The PCR amplification is preferably conducted in the presence of an internal control for the detection of Taq inhibitors. For example, a plasmid containing a sequence, also not human-related, amplifiable with the set of primers used in the amplification of the target DNA, may be added to the PCR reaction mixture. This internal control allows to prevent false negative results due to the presence of Taq inhibitors.

In order to determine the quantity of each amplicon it is necessary to prepare a calibration curve by amplifying known dilutions of genomic DNA or plasmids containing the nucleotide sequences of the target DNA fragments, using the same primers and the same conditions of the test samples. For example, when an automatic fragment sequencer/analyser is used, the AUC (Area Under the Curve) values obtained from the amplification of known quantities of DNA are plotted in a calibration curve; the amounts of DNA in the test samples are then interpolated on the same curve.

The total quantity of the amplification products corresponding to different fragments (i.e. the sum of single amplicon amounts), expressed in weight units, is then compared with a reference or "cut-off" value previously determined on the basis of case series comprising healthy subjects and patients in whom the presence of colorectal tumours or lesions has been established. These cases must include a sufficient number of patients and controls to provide a good confidence interval (CI 95%), preferably at least 50 patients and 50 healthy volunteers.

The accuracy, sensitivity and specificity of the method make it particularly useful in the early diagnosis of colorectal tumours, and in the evaluation of the risk or probability of developing such tumours in persons with pre-cancerous colorectal lesions. Further advantages of the method are its simplicity, speed and low cost.

Another aspect of the invention relates to a kit suitable for carrying out the method described above. The kit may contain labelled oligonucleotides, thermostable DNA polymerase, solutions and reagents for the performance of a PCR reaction and for a quantitation assay (e.g. the immunoenzyme or fluorimetric method). The kit can also contain instructions on the correct operating method.

FIGS. 1-3: EXAMPLES OF FL-DNA ANALYSIS

FIGS. 2a, 2b and 2c.

MATERIAL AND METHODS

DNA Purification

Approximately 4 g of stool were thawed at room temperature. DNA was extracted after a 15-min homogenization with 16 ml of TE-9 buffer pH 9 (0.5 M Tris-HCl, 20 mM EDTA and 10 mM NaCl) by ULTRA-TURRAX T25™ (Janke & Kunkel GmbH Co. KG IKA-Labortechnik, Staufen, Germany). After centrifugation at 5,000 g for 15 min, the supernatant was transferred to a tube containing 5 ml of 7.5 M ammonium acetate (M-Medical, Florence, Italy) and 30 ml of 100% ethanol (Carlo Erba, Milan, Italy). DNA was recovered by centrifugation at 5,000 g for 15 mm at room temperature. Stool samples were suspended in 1.6 ml of ASL buffer and DNA was extracted using the QIAamp DNA Stool Kit (QIAGEN™, Hilden, Germany).

FL-DNA Analysis

Amplifications of exons 5-8 of p53 and fragments 1-4 of APC exon 15 were carried out on 2 µl of DNA from stool in a total volume of 25 µl containing 0.4 µM of each primer, 200 µM of deoxynucleotide triphosphates, 1x reaction buffer with 3.5 mM MgCl2 and 1 unit of Taq polymerase (QIAGEN™). The reaction mixture was subjected to 32 cycles: 60s at 94° C. and then 60s at 60 ° C. for p53 exons, and 58° C. for APC fragments, followed by incubation at 72° C. for 60s.

The p53 exons were amplified simultaneously in a single reaction mixture and the 4 APC fragments were amplified in two different mixes (mix 1—fragments 1 and 2; mix 2—fragments 3 and 4). For this purpose, primers used for L-DNA analysis were end-labelled with fluorochromes provided by Applied Biosystems (Foster City, Calif.).

Amplification 1: exons from 5 to 8 of p53 gene (Gene Bank n. X54156, nt. 13042-13253, 13308-13489, 13986-14124, 14404-14603). Amplification 1 and 2: fragments corresponding to aminoacids 862-954 and 1035-1130 of exon 15 of APC gene (Gene Bank AF127506, M74088). Amplification 3 and 4: fragments corresponding to aminoacids 1288-1402 and 1421-1515 of exon 15 of APC gene (Gene Bank AF127506, M74088).

| P53 Exons | Primer name | 5'-labelling | Sequence | SEQ ID NO: |
|---|---|---|---|---|
| 5 | 5-F | 6-FAM- ™ | ctcttcctgcagtactccctgc | 1 |
|   | 5-R |  | gccccagctgctcaccatcgcta | 2 |
| 6 | 6-F |  | gattgctcttaggtctggcccctc | 3 |
|   | 6-R | HEX ™ | ggccactgacaaccacccttaacc | 4 |
| 7 | 7-F | 6-FAM ™ | gcgttgtctcctaggttggctctg | 5 |
|   | 7-R |  | caagtggctcctgacctggagtc | 6 |
| 8 | 8-F |  | acctgatttccttactgcctctggc | 7 |
|   | 8-R | HEX ™ | gtcctgcttgcttacctcgcttagt | 8 |

| APC Fragment | Primer name | 5'-labelling | Sequence | SEQ ID NO: |
|---|---|---|---|---|
| 1 | 1BF |  | aactaccatccagcaacaga | 9 |
|   | 1BR | HEX ™ | taatttggcataaggcatag | 10 |
| 2 | 2F | 6-FAM ™ | cagttgaactctggaaggca | 11 |
|   | 2R |  | tgacacaaagactggcttac | 12 |
| 3 | 3F |  | gatgtaatcagacgacacag | 13 |
|   | 3R | HEX ™ | ggcaatcgaacgactctcaa | 14 |
| 4 | 4F | 6-FAM ™ | cagtgatcttccagatagcc | 15 |
|   | 4R |  | aaatggctcatcgaggctca | 16 |

Electrophoresis was carried out using a 3100Avant Genetic Analyzer (Applied Biosystems) equipped with GeneScan Analysis 3.7.

Figure 1A:
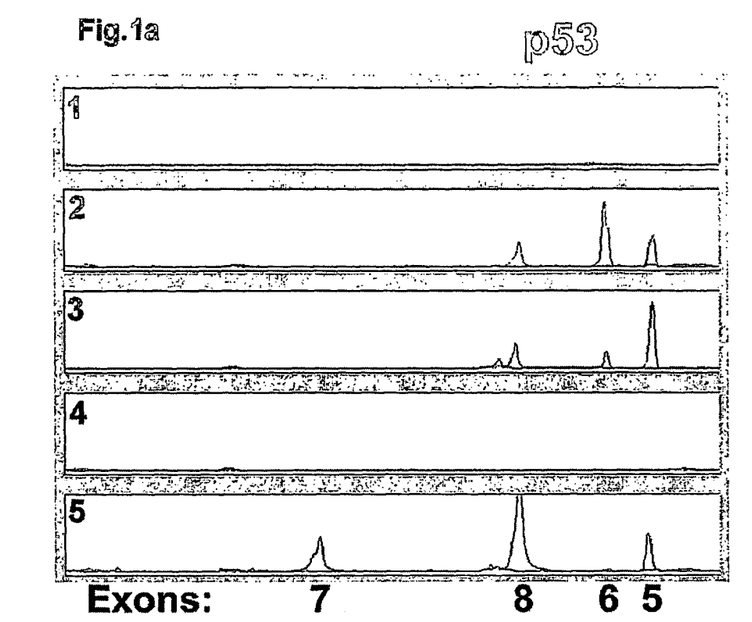
FIGS. 1a and 1b: DNA extracted from stool samples. The FL-DNA (Fluorescence long DNA) for each sample is given by the sum of the amounts (ng) of three groups of amplicons: p53—exons 5-8, APC fragments 1-2 and 3-4.
Figure 1B:
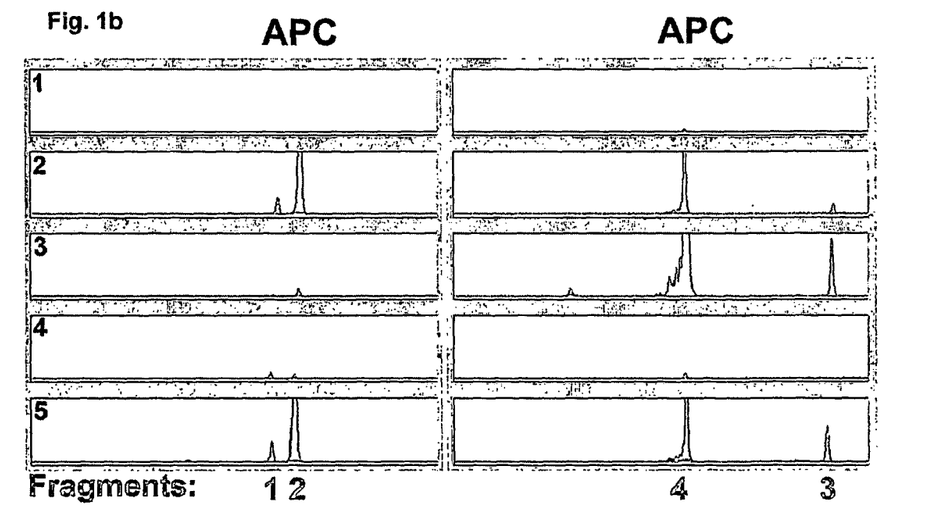
Figure 2A:
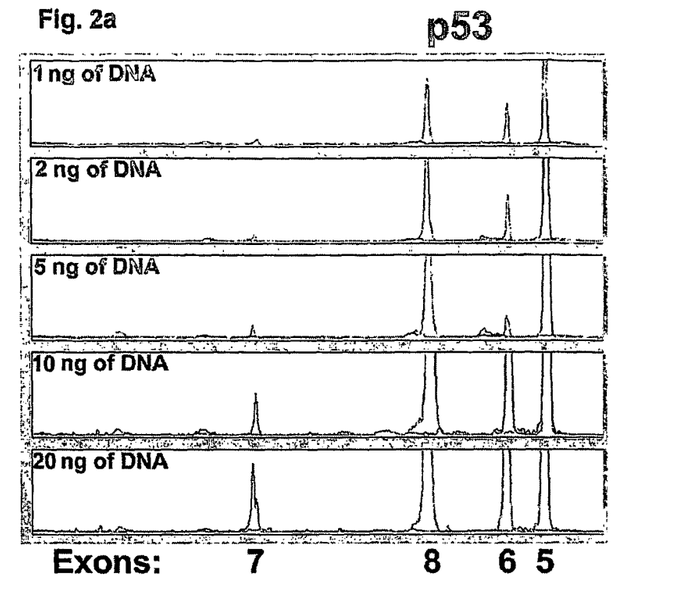
FIG. 2a and FIG. 2b are electropherograms for each sample obtained by amplification of known DNA amounts. The AUC values from FIG. 2a and FIG. 2b are normalized (area/100*ng) and plotted against the DNA amount (1, 2, 5, 10 and 20 ng) in the corresponding calibration curves of FIG. 2c. The levels of amplification of each sample—expressed in weight units (nanograms)—are determined from these corresponding calibration curves.
Figure 2B:
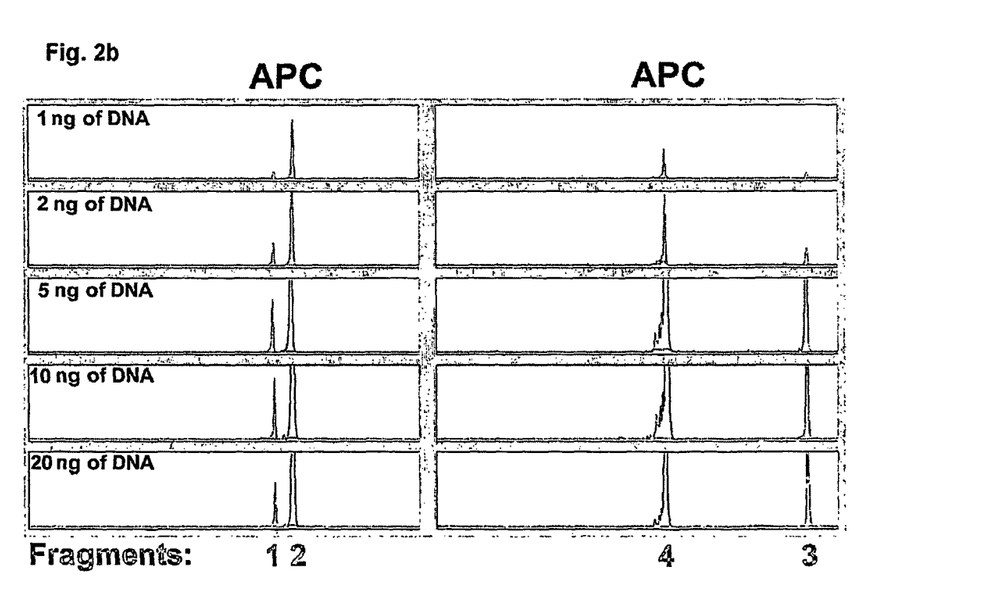
Figure 2C:
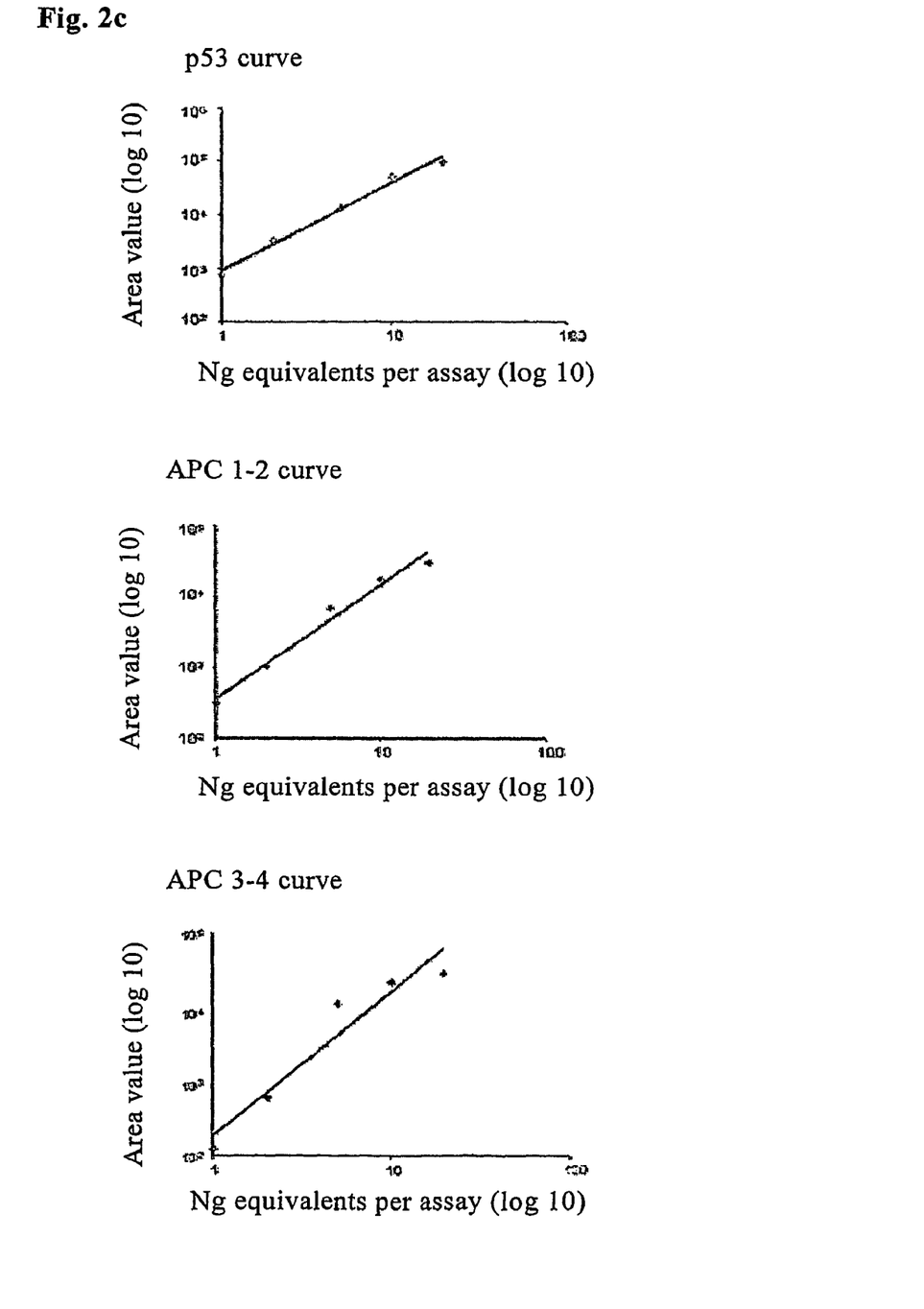

FL-DNA was performed by analyzing the fluorescence intensity of each sample-specific PCR product (FIG. 1ab). The quantification of each sample was calculated by reference to a standard curve (1, 2, 5, 10 and 20 ng) of genomic DNA and expressed as nanograms (FIG. 2abc). To verify the presence or absence of Taq inhibitors, an amplification was performed on all samples with a mix containing 2 µl of DNA extracted from stool and 25 attograms [ag] of a plasmid with a control sequence. All determinations were performed in duplicate and repeated in about 20% of samples in which the variation was >20%.

Case Series

Stool samples from 86 patients with primary colorectal cancer were collected in the Gastroenterology Unit and Dept. of Surgery I, Morgagni Hospital, Forli and in the Depts. of Oncology and General Surgery, Infermi Hospital, Rimini. Stool samples were collected from 62 individuals who proved negative for cancer or benign lesions after colonoscopy, and from laboratory personnel.

Stool samples were obtained at least three days after the administration of laxative treatments in preparation for colonoscopy to allow for the recovery of normal bowel functionality. The fecal specimens were immediately frozen and stored at −70° C. for a maximum of two months.

Cancer diagnosis was histologically confirmed and pathological stage was defined according to Dukes' classification: 8 tumors were classified as stage A, 30 as stage B, 37 as stage C and 9 as stage D. Moreover, 19 cancers were located in ascending, 30 in descending, 2 in transverse colon and 35 in the rectal tract. Staging information was not available for only two cases.

Of the 86 patients, 42 were male and 44 were female and median age was 72 years (range 36-90). Of the 62 controls, 29 were male and 33 female and median age was 51 years (range 21-87).

Results

Fluorescence signals ranged from 0 to 283 ng (median 47 ng) in patient stool and from 0 to 87 ng (median 4 ng) in healthy donor stool. No differences in median values were observed with respect to age of patients and size, site and stage of tumor.

When the results from the two approaches were compared, a direct relation was observed, but with a wide variability of FL-DNA levels within the subgroups defined according to the number of L-DNA high amplifications. Moreover, fluorescence by FL-DNA method was detected in 33 out of the 47 individuals who did not show any high amplification by L-DNA assay. These results are clearly indicative of a higher sensitivity of the fluorescence method than of the conventional approach.

Figure 3:
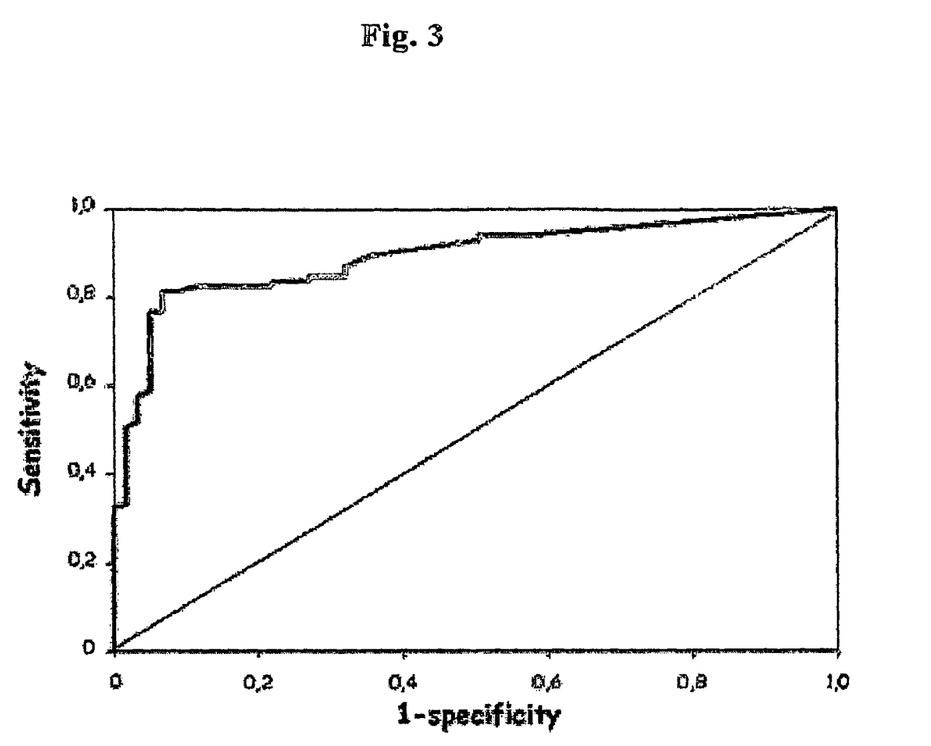
FIG. 3: ROC curve of FL-DNA analysis of stool samples from patients and healthy donors.

The ROC curve analysis of FL-DNA levels (FIG. 3) shows a good diagnostic accuracy of this approach. In particular, very high specificity ranging from 83% to 95% and high sensitivity ranging from 82% to 72% were observed for the most discriminant cut-offs of 15, 20, 25 and 30 ng of DNA (Table 1). When the cut-off of 25 ng, which provides the best overall accuracy, was analyzed in relation to the different tumor characteristics, sensitivity remained high in patients with small (70%) compared to large tumors (82%) and was similar for the different Dukes' stage tumors (Table 2). More importantly, a similar sensitivity was observed in detecting tumors localized in ascending and descending colon tracts.

TABLE 1

Sensitivity and specificity of FL-DNA analysis

| DNA LEVELS Cut-off (ng) | HEALTHY DONORS Positive | Negative | PATIENTS Positive | Negative | Sensitivity % | C.I. 95% | Specificity % | C.I. 95% |
|---|---|---|---|---|---|---|---|---|
| 15 | 10 | 49 | 70 | 15 | 82 | (74-90) | 83 | (73-93) |
| 20 | 7 | 52 | 70 | 15 | 82 | (74-90) | 88 | (80-96) |
| 25 | 4 | 55 | 65 | 20 | 76 | (67-85) | 93 | (86-100) |
| 30 | 3 | 56 | 61 | 24 | 72 | (62-82) | 95 | (89-100) |

TABLE 2

Sensitivity* as a function of different characteristics in colorectal cancer

| Category | No. PATIENTS | POSITIVE | NEGATIVE | SENSITIVITY % |
|---|---|---|---|---|
| SIZE (cm) | | | | |
| 0.1-4.0 | 40 | 28 | 12 | 70 |
| ≧4.1 | 38 | 31 | 7 | 82 |
| DUKES' STAGE | | | | |
| A | 8 | 7 | 1 | 88 |
| B | 29 | 25 | 4 | 86 |
| C | 37 | 25 | 12 | 68 |
| D | 9 | 8 | 1 | 89 |
| LOCATION | | | | |
| Ascending | 18 | 13 | 5 | 72 |
| Transverse | 2 | 2 | 0 | 100 |
| Descending | 30 | 22 | 8 | 73 |
| Rectum | 35 | 28 | 7 | 80 |

*Cut off value 25 ng

References (1) Parkin D M, Whelan S L, Ferlay J, Raymond L, Young J, editors. Cancer incidence in five countries. IARC Scientific Publications No. 143. Lyon: International Agency for Research on Cancer; 1997.

(2) Boyle P. Faecal occult blood testing (FOBT) as screening for colorectal cancer: the current controversy. Ann Oncol 2002; 13:16-8.

(3) Strul H, Arber N. Fecal occult blood test for colorectal cancer screening. Ann Oncol 2002; 13:51-6.

(4) Ries L A G, Eisner M P, Kosary C L, Hankey B F, Miller B A, Clegg L, et al., editors. SEER Cancer Statistics Review, 1975-2000. Bethesda (MD): National Cancer Institute; 2003. Available from: URL: http://seer.cancer-.gov/csr/1975_2000, 2003.

(5) Levin B, Brooks D, Smith R A, Stone A. Emerging technologies in screening for colorectal cancer: CT colonography, immunochemical fecal occult blood tests and stool screening using molecular markers. CA Cancer J Clin 2003; 53:44-55.
(6) Sidransky D, Tokino T, Hamilton S R, Kinzler K W, Levin B, Frost P, et al. Identification of ras oncogene mutations in the stool of patients with curable colorectal tumors. Science 1992; 256:102-5.
(7) Hasegawa Y, Takeda S, Ichii S, Koizumi K, Maruyama M, Fujii A, et al. Detection of K-ras mutations in DNAs isolated from feces of patients with colorectal tumors by mutant-allele-specific amplification (MASA). Oncogene 1995; 10:1441-5.
(8) Smith-Ravin J, England J, Talbot C, Bodmer W. Detection of c-Ki-ras mutations in faecal samples from sporadic colorectal cancer patients. Gut 1995; 36:81-6.
(9) Villa E, Dugani A, Rebecchi A M, Vignoli A, Grottola A, Buttafoco P, et al. Identification of subjects at risk for colorectal carcinoma through a test based on K-ras determination in the stool. Gastroenterology 1996; 110:1346-53.
(10) Nollau P, Moser C, Weinland G, Wagener C. Detection of K-ras mutations in stools of patients with colorectal cancer by mutant-enriched PCR. Int J Cancer 1996; 66:332-6
(11) Puig P, Urgell E, Capella G, Sancho FJ, Pujol J, Boadas J, et al. A highly sensitive method for K-ras mutation detection is useful in diagnosis of gastrointestinal cancer. Int J Cancer 2000; 85:73-7.
(12) Prix L, Uciechowski P, Bockmann B, Giesing M, Schuetz AJ.
Diagnostic biochip array for fast and sensitive detection of K-ras mutation in stool. Clin Chem 2002; 48:428-35.
(13) Eguchi S, Kohara N. Komuta K, Kanematsu T. Mutations of the p53 gene in the stool of patients with resectable colorectal cancer. Cancer 1996; 77:1707-10.
(14) Deuter R, Muller 0. Detection of APC mutation in stool DNA of patients with colorectal cancer by HD-PCR. Hum Mutat 1998; 11:84-9.
(15) Traverso G, Shuber A, Levin B, Johnson C, Olsson L, Schoetz D J Jr, et al. Detection of APC mutations in fecal DNA from patients with colorectal tumors. N Engl J Med 2002; 346:311-20.
(16) Traverso G, Shuber A, Olsson L, Levin B, Johnson C, Hamilton SR, et al. Detection of proximal colorectal cancer through analysis of faecal DNA. Lancet 2002; 359:403-4.
(17) Rengucci C, Maiolo P, Saragoni L, Zoli W, Amadori D, Calistri D.
Multiple detection of genetic alterations in tumors and stool. Clin Cancer Res 2001; 7:590-3.
(18) Dong S M, Traverso G, Johnson C, Geng L, Favis R, Boynton K, et al. Detecting colorectal cancer in stool with the use of multiple genetic targets. J Natl Cancer Inst 2001; 93:858-65.
(19) Ahlquist D A, Skoletsky J E, Boynton K A, Harrington J J, Mahoney D W, Pierceall W E, et al. Colorectal cancer screening by detection of altered human DNA in stool: feasibility of a multitarget assay panel. Gastroenterology 2000; 119:1219-27.
(20) Tagore K S, Lawson M J, Yucaitis J A, Gage R, Orr T, Shuber A P, et al. Sensitivity and specificity of a stool DNA multitarget assay panel for the detection of advanced colorectal neoplasia. Clin Colorectal Cancer 2003; 3:47-53.
(21) Calistri D, Rengucci C, Bocchini R, Saragoni L, Zoli W, Amadori D. Fecal multiple molecular tests to detect colorectal cancer in stool. Clin Gastr Hep 2003; 1:377-83.

The invention claimed is:

1. A method based on fluorescence long (FL-DNA) analysis for determining the presence of colorectal tumors in a human subject, which comprises:

a) extracting DNA from human stool samples;

b) amplifying by PCR:

i) p53 gene fragments corresponding to exons 5-8 using the following pairs of primers labeled with fluorescent markers:

```
1)       ctcttcctgcagtactccctgc              (SEQ ID NO: 1)
and
         gccccagctgctcaccatcgcta,             (SEQ ID NO: 2)

2)       gattgctcttaggtctggcccctc             (SEQ ID NO: 3)
and
         ggccactgacaaccacccttaacc,            (SEQ ID NO: 4)

3)       gcgttgtctcctaggttggctctg             (SEQ ID NO: 5)
and
         caagtggctcctgacctggagtc,             (SEQ ID NO: 6)

4)       acctgatttccttactgcctctggc            (SEQ ID NO: 7)
and
         gtcctgcttgcttacctcgcttagt,           (SEQ ID NO: 8)
``` ii) APC gene fragments using the following pairs of primers labeled with fluorescent markers:

```
1)       aactaccatccagcaacaga                 (SEQ ID NO: 9)
and
         taatttggcataaggcatag,                (SEQ ID NO: 10)

2)       cagttgaactctggaaggca                 (SEQ ID NO: 11)
and
         tgacacaaagactggcttac,                (SEQ ID NO: 12)

3)       gatgtaatcagacgacacag                 (SEQ ID NO: 13)
and
         ggcaatcgaacgactctcaa,                (SEQ ID NO: 14)

4)       cagtgatcttccagatagcc                 (SEQ ID NO: 15)
and
         aaatggctcatcgaggctca;                (SEQ ID NO: 16)
``` c) quantifying the amplified fragments and identifying the amplified fragments as amplicons;

d) calculating the total amount of different amplicons; and e) comparing the total amount of amplicons with a reference value determined on the basis of a case series comprising healthy subjects and patients affected by colorectal tumors, wherein a total amount of amplicons higher than the reference value is indicative of the presence of colorectal tumors in said human subject.

2. The method according to claim 1, wherein the amplicon quantities are interpolated on a calibration curve obtained from known DNA amounts.

3. The method according to claim 1, wherein the amplicons are quantified with an automatic sequencer/analyser or using fluorometric or spectrophotometric detection systems.

* * * * *

SEQUENCE LISTING

```
<160> NUMBER OF SEQ ID NOS: 16

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcttcctgc agtactcccc tgc                                                 23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccccagctg ctcaccatcg cta                                                 23

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
gattgctctt aggtctggcc cctc                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggccactgac aaccaccctt aacc                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgttgtctc ctaggttggc tctg                                          24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caagtggctc ctgacctgga gtc                                           23

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acctgatttc cttactgcct ctggc                                         25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtcctgcttg cttacctcgc ttagt                                         25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aactaccatc cagcaacaga                                                      20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taatttggca taaggcatag                                                      20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cagttgaact ctggaaggca                                                      20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgacacaaag actggcttac                                                      20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gatgtaatca gacgacacag                                                      20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcaatcgaa cgactctcaa                                                      20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cagtgatctt ccagatagcc                                                      20

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaatggctca tcgaggctca                                                  20
```